US012561309B2

(12) United States Patent
Schroeter et al.

(10) Patent No.: US 12,561,309 B2
(45) Date of Patent: Feb. 24, 2026

(54) CORRELATION OF HETEROGENOUS MODELS FOR CAUSAL INFERENCE

(71) Applicant: 342022, Inc., Newcastle, WA (US)

(72) Inventors: John Schroeter, Bainbridge Island, WA (US); Frederic L. Sax, Estero, FL (US)

(73) Assignee: 342022, Inc., Newcastle, WA (US)

( * ) Notice: Subject to any disclaimer, the term of this patent is extended or adjusted under 35 U.S.C. 154(b) by 0 days.

(21) Appl. No.: 18/372,589

(22) Filed: Sep. 25, 2023

(65) Prior Publication Data

US 2024/0104084 A1 Mar. 28, 2024

Related U.S. Application Data

(60) Provisional application No. 63/410,554, filed on Sep. 27, 2022.

(51) Int. Cl.
*G06F 16/23* (2019.01)
*G16H 10/20* (2018.01)

(52) U.S. Cl.
CPC ......... *G06F 16/2365* (2019.01); *G16H 10/20* (2018.01)

(58) Field of Classification Search
CPC ............................ G06F 16/2365; G16H 10/20
See application file for complete search history.

(56) References Cited

U.S. PATENT DOCUMENTS

| | | | | |
|---|---|---|---|---|
| 10,496,678 B1 * | 12/2019 | Tang | .......................... | G06F 16/29 |
| 10,546,245 B2 | 1/2020 | Virkar et al. | | |
| 11,055,891 B1 * | 7/2021 | Ofek | .......................... | G06T 13/40 |
| 11,450,412 B1 * | 9/2022 | Mohiuddin | ............ | G16H 10/60 |

(Continued)

FOREIGN PATENT DOCUMENTS

| | | |
|---|---|---|
| JP | 2023508466 A | 12/2023 |
| KR | 20110003352 A | 1/2011 |

(Continued)

OTHER PUBLICATIONS

International Application No. PCT/US2023/033752, International Search Report and Written Opinion mailed Jan. 22, 2024, 9 pages.

(Continued)

*Primary Examiner* — Khanh B Pham
*Assistant Examiner* — Brooks T Hale
(74) *Attorney, Agent, or Firm* — Conley Rose, P.C.

(57) ABSTRACT

A causal inference engine relies on a category database and a graph database. Via a loader, a category generator, and a spatial web generator, input data is received in disparate formats and converted into a normalized attribute vector comprising a mathematical model, experiment, experimental data, and miscellaneous attributes. The normalized attribute vectors are then loaded into a category database and a graph database. Specifically, the loader makes use of a multi-formal combinatorial parser, and an ontology store to convert the different data and formats into normalized attribute vectors. The category generator reviews mathematical model attributes in the normalized attribute vectors to associate vectors into mathematical categories. The spatial web generator performs similarity scores in the attributes of the vectors to determine placement in a graph database. The data in the category database and the graph database are then utilized by the causal inference engine to perform inferences.

19 Claims, 5 Drawing Sheets

400

(56) References Cited

U.S. PATENT DOCUMENTS

| | | | |
|---|---|---|---|
| 11,804,282 B1 * | 10/2023 | Aravamudan | G16H 20/10 |
| 2002/0169730 A1 | 11/2002 | Lazaridis | |
| 2010/0299335 A1 | 11/2010 | Gopalakrishnan et al. | |
| 2011/0109435 A1 * | 5/2011 | Bickel | G01C 21/3679 |
| | | | 340/8.1 |
| 2013/0238642 A1 | 9/2013 | Clayton et al. | |
| 2014/0244631 A1 * | 8/2014 | Arthur | G06F 16/43 |
| | | | 707/723 |
| 2015/0286802 A1 | 10/2015 | Kansara | |
| 2016/0065597 A1 * | 3/2016 | Nguyen | H04L 63/1441 |
| | | | 726/22 |
| 2016/0132787 A1 * | 5/2016 | Drevo | G06N 20/10 |
| | | | 706/12 |
| 2016/0253480 A1 * | 9/2016 | Comish | G16H 10/20 |
| | | | 705/3 |
| 2016/0321407 A1 | 11/2016 | Muñoz-Jiménez et al. | |
| 2018/0096105 A1 | 4/2018 | Bleicher et al. | |
| 2018/0107763 A1 | 4/2018 | Chen et al. | |
| 2019/0361908 A1 | 11/2019 | Lee et al. | |
| 2021/0257049 A1 | 8/2021 | Abeliuk et al. | |
| 2021/0288925 A1 * | 9/2021 | Tagra | H04L 51/04 |
| 2021/0366581 A1 | 11/2021 | Lee et al. | |
| 2022/0261538 A1 * | 8/2022 | Berns | G06F 40/205 |

FOREIGN PATENT DOCUMENTS

| | | | |
|---|---|---|---|
| KR | 20120093972 A | 8/2012 |
| KR | 20200054203 A | 5/2020 |
| WO | 2019022779 A1 | 1/2019 |
| WO | 2021186196 A1 | 9/2021 |

OTHER PUBLICATIONS

Luo, Gang and John Schroeter. Automatic and Transparent Machine Learning. The New Popular Electronics, vol. 1, No. 1 (Dec. 10, 2017), pp. 198-206 [retrieved on Sep. 15, 2022]. Retrieved from the Internet: https://popularelectronics.technicacuriosa.com/2017/12/10/popular-electronics.

International Application No. PCT/US2024/022889, International Search Report and Written Opinion mailed Jul. 16, 2024, 17 pages.

International Application No. PCT/US2023/033751, International Search Report and Written Opinion mailed Jan. 22, 2024, 11 pages.

U.S. Appl. No. 18/626,149, Office Action mailed Jun. 12, 2025, 14 pages.

Mirzaei et al., A Machine Learning Tool to Predict the Antibacterial Capacity of Nanoparticles. Nanomaterials (Basel). Jul. 7, 2021;11(7):1774. doi: 10.3390/nano11071774. PMID: 34361160; PMCID: PMC8308172 (Year: 2021).

* cited by examiner

400

500

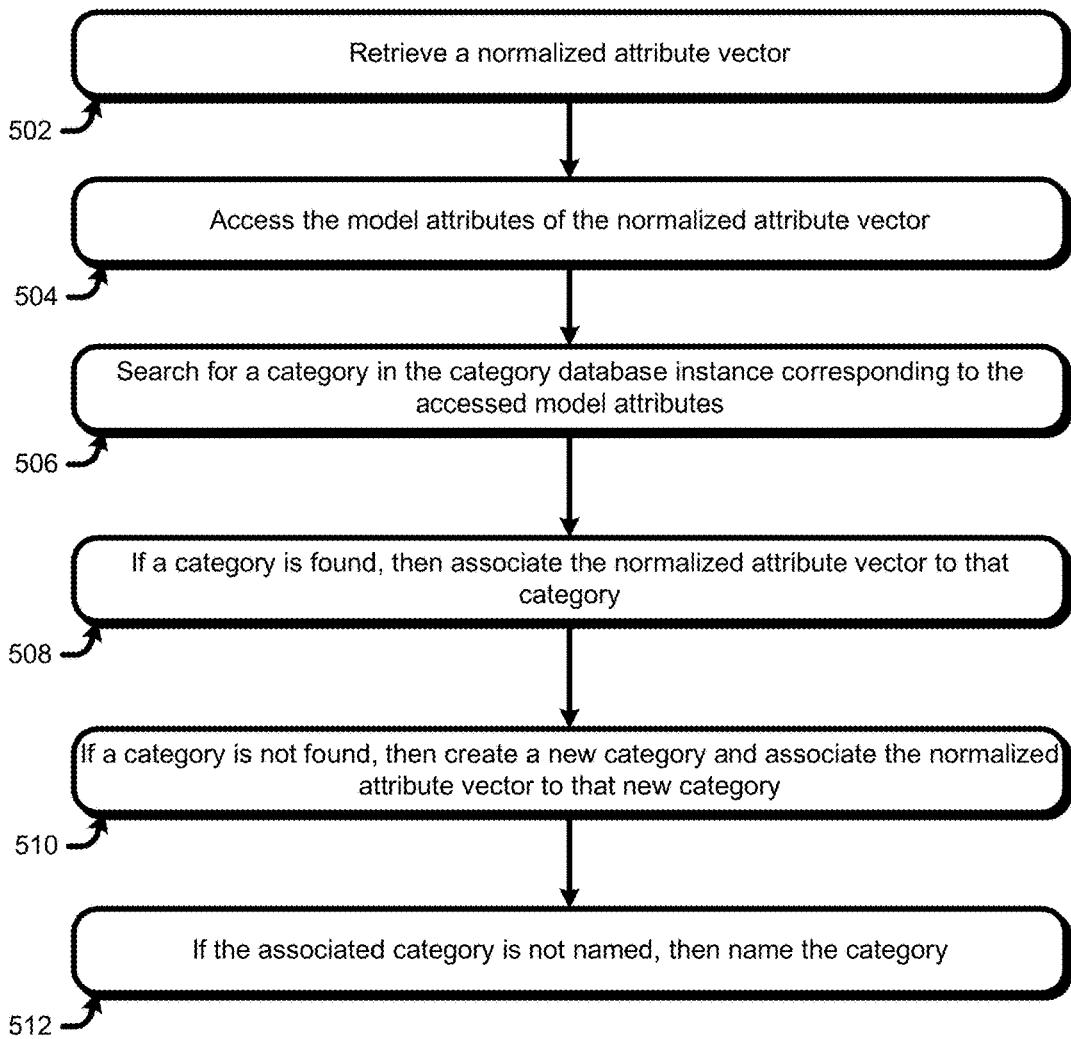

Retrieve a normalized attribute vector

502

Access the model attributes of the normalized attribute vector

504

Search for a category in the category database instance corresponding to the accessed model attributes

506

If a category is found, then associate the normalized attribute vector to that category

508

If a category is not found, then create a new category and associate the normalized attribute vector to that new category

510

If the associated category is not named, then name the category

CORRELATION OF HETEROGENOUS MODELS FOR CAUSAL INFERENCE

CROSS-REFERENCE TO RELATED APPLICATION

This application claims priority to U.S. application Ser. No. 63/410,554, filed on Sep. 27, 2022, and titled "COR-RELATION OF HETEROGENOUS MODELS FOR CAUSAL INFERENCE," the entire disclosure of which is incorporated herein by reference.

BACKGROUND

At any one point in time, a huge amount of research and development is being performed at universities, public laboratories, private laboratories, commercial companies, and any number of other institutions. There is tremendous overlap between experiments and other trials being performed, but often the data from these experiments and trials are not systematically correlated or otherwise leveraged. Unless a researcher affirmatively does so, results from one trial are often not used to supplement the results of another. Accordingly, data that could strengthen the accuracy and quality of a research effort goes unleveraged.

In order for a researcher to leverage another's experimental data, that researcher not only needs to know of the other experiment, but also that the other experimental data is in fact applicable to the researcher's original experiment. Different experiments have different protocols, different models, different data formats, and the like. Accordingly, it is not a trivial exercise to determine whether the results of one experiment are applicable to another, let alone how to make those results correlate.

The scientific research involved in the discovery and testing of new medical entities is a particular instance of research for which the need to correlate data from different experiments and trials is more exigent. In the case of clinical trials, such as for drug discovery and testing, experiments are being performed on human beings, many of which have otherwise untreatable illnesses. During a trial, a patient is being told that the medication might do nothing (i.e., be placebo), make things worse (i.e., be ineffective), or maybe, just maybe, might make them better. From this context, extracting the maximum value from data goes beyond the needs of making science effective, rather it is exigent from a humanitarian perspective.

Accordingly, there is a need to discover experiments that may relate to other experiments, determine transformations on how to correlate materials and data from different experiments, and to determine what conclusions may be drawn from the correlated materials and data.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

FIG. 5 is a flow chart for identifying categories from normalized attribute vectors.

DETAILED DESCRIPTION

Figure 1:
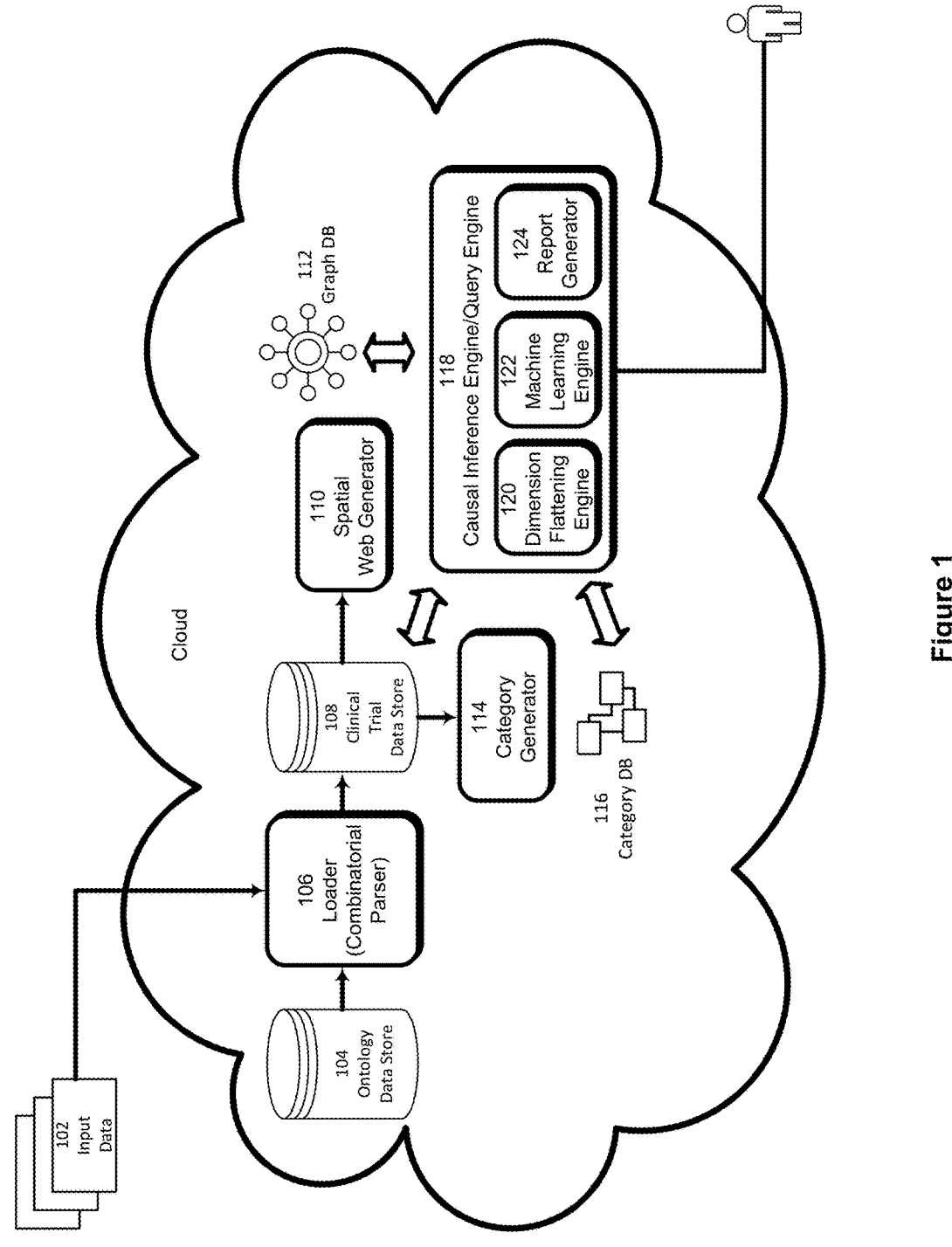
FIG. 1 is a context diagram for correlation of heterogenous models for causal inference.

The Context of Correlation of Heterogenous Models for Causal Inference

Overview of Models

In scientific method, one generally has a model to validate, where the model often has a set of parameters that represent the state of the model, and a set of rules relating those parameters. An experimenter will make a hypothesis around a model, will design an experiment on how to perturb one or more of those parameters and make observations in an attempt to verify (or intentionally contradict in order to disprove) the hypothesis, and ultimately some aspect of the model.

Models are well known in science. Parameters in mechanical physics include time, position, and mass. The state model has been extended to include non-time dependent parameters including momentum, force, energy, and work, and time dependent parameters including velocity, acceleration, and power. In some cases, parameters are statistically independent, or can be statistically dependent (i.e., derived from other parameters, e.g., velocity may be expressed as a first derivative of position, and force may be expressed as a first derivative of momentum).

Time dependent models are "dynamic" and are sometimes called "dynamical systems." The study of dynamical systems generally involves one or more ordinary differential equations (ODEs) and/or partial differential equations (PDEs).

By way of example, clinical trials for drug discovery and testing can be evaluations of dynamical systems. For example, consider pharmacokinetic models, which are models of how a substance, for example a drug, is liberated from its respective delivery system, absorbed into a subject, distributed through different tissues and organs of the subject, metabolized by the subject, eliminated from the subject, and the substance's general impact on the subject, such as a drug patient. Specifically, drug absorption by a person is a function of time, and therefore is dynamic. Since drug distribution, metabolism, and excretion are functions of drug absorption (and other time dependent factors), those aspect are also dynamic. As a result, many models under test in clinical trials, including pharmacokinetic models, are comprised of differential equations, many differentiated over time.

Because clinical trials are heterogenous, that is they have different models with different underlying assumptions, it's unclear how to relate those models. For example, some pharmacokinetic models assume a single or multi-compartment model of the body, and others assume no compartments at all. In compartment models, the body is subdivided into one or more compartments, and substances are seen as propagating through those compartments. Given this degree of interactive complexity across the varying trials and research, a capability that allows correlation and causal inference across heterogenous models would be a substantive improvement over any prior art.

Described herein are systems and methods for a causal inference engine that among other things makes use of category theory and dimensional flattening techniques such as with a spatial web to relate heterogenous clinical trials.

Before discussing the causal inference engine, we will discuss category theory and dimensional flattening.

Overview of Category Theory—Categories, Functors, Natural Transformations

One approach to relate what on the surface appear to be incompatible models is to make use of category theory. Category theory is a discipline of mathematics used to relate different mathematical representations. Specifically, mathematical structures, usually abstract algebraic structures, can be organized into categories. Relationships between categories are called functors, and relationships between functors are called natural transformations.

Before turning to categories with respect to causal inference, some pedagogical examples for categories may be in order. Consider two kinds of algebraic structures, first is the group (a set with a binary operation, the set supporting an identity and an inverse over the operation), and a field, (a set with two binary operations, the set supporting an identity and an inverse for each operation). A typical example of a group is the set of integers over addition (the number zero being the identity and subtraction being the inverse). A typical example of a field is the set of real numbers over addition and multiplication. The real numbers support addition in the same way integers do, and the real numbers support multiplication (the number one being the identity and division being the inverse). We say that integers over addition is an object in the category of Groups. Similarly, we say that reals over addition and multiplication is an object in the category of Fields.

The consequence is that two objects being in the same category suggests that a transformation exists to map objects from one object to the other object in a property-preserving way.

In general, mappings are not guaranteed to preserve all properties. For example, a scaling matrix transformation of two-dimensional shape preserves angles but not necessarily distances. It is of interest to identify what properties are indeed preserved across mappings. Specifically, if a first pharmacokinetic model belongs to a first category, and a second pharmacokinetic model belongs to a second category, those models by definition are mathematically heterogenous. The ability to correlate those two heterogenous models relies on the existence of mappings that preserve the properties of those models that experimenters are measuring.

An example is mathematical composition. Recall from algebra that composition of functions involves taking two functions and creating a third function by chaining those two functions. By way of example, within R→R functions (real numbers to real numbers), f(x) and g(x), h(x)=f(g(x)) is an example of composition of functions. Generalizing to category theory, mappings can be composed in the same way, and have identities and are associative.

Note that computer programming can be modeled as a series of compositions. Indeed, the functional programming paradigm is generally performed as a series of compositions and recursions. The consequence is that there are categories called monads that support such chaining via composition, and therefore support mathematical formalisms of programming Turning to applications of scientific inquiry and working with heterogenous models, note that a first model and a second model, can belong to a first category and a second category respectively. Functors and natural transformations (described in further detail below) help identify mappings that are property-preserving and can be composed, thereby enabling operations on the two heterogenous models despite being in different categories. In the case of clinical trials, note that pharmacokinetic models are oft characterized as a dynamic system comprised of a set of time dependent ordinary differential equations. One can work directly with the differential equations, or one can make use of functionality as informed by monads as to what compositions can be made between the two heterogenous models.

Functors represent mappings between categories. Note that functors can map items in a category to that same category. Alternatively, functors can map between two categories. Functors can be used as a means of property-preserving transformations between a structure in one category and a structure in another category.

The consequence is that if a first object is in one category and a second object is in another category, and a functor between the categories can be identified, this suggests that a transformation exists to map objects from the first object to the second object in a property-preserving way.

In fact, two categories C1 and C2, can be related as a form of weak equivalence, if a type of functor, called a left adjoint functor maps from C1 to C2 and another type of functor, called a right adjoint functor, maps from C2 to C1. The consequence is that objects in these two categories may be mixed and matched provided that transformations satisfying the identified adjoint functors are honored.

Functors themselves can be transformed in such a way to preserve properties. Such transformations are called natural transformations. The consequence is that functors and natural transformations may be used to identify how to construct transformations including via composition.

The foregoing is a very brief outline of category theory, and is not intended to be limiting, but rather to introduce terms used in this disclosure.

Applying Category Theory to Relate Models

Turning to the relation of models, consider where a first model used in a first experiment is in a first category and a second model used in a second experiment is in a second category. If a functor can be identified between the two categories, then a mapping may be identified that maps elements, such as state variables, and operations within the model, of the first model to elements of the second model.

In the case of where the first category is the same category as the second category, category theory need not be used. However, for algorithms relying on category theory, the identity functor, which is a functor mapping from a category to the same category, and making no changes, may be made use of.

In the case where the first category and the second category are different, functors mapping two categories may be used to identify transformations between the first model and the second model, and to identify what properties are preserved across transformation. In this way results from a first model can be applied to a second model, even if the two models are in mathematically different structures. Where natural transformations exist between functors between the same two categories, techniques to refine transformational mappings between the two categories, such as composition.

Additionally, where adjoint functors exist between the two categories, this suggests that some well-defined subset of results from the two models may be aggregated together.

To be clear, data or results from different models need not be combined in their entirety. Rather, properties that represent model state parameters that in turn can demonstrate correlation, or preferably causation should be preserved. The notion of causal inference is the notion that a machine, in particular a computer, can look at a set of data and/or information, and determine whether a relationship between properties is causal. Note that correlation (as opposed to causation) is a mathematical relationship. Specifically, if one can show that one statistical variable is a dependent variable with respect to an independent variable (i.e., the dependent variable is a function of the independent variable), one can demonstrate correlation. However, causation involves semantic analysis, that is to say there is a real-world mechanism that is in fact modeled by mathematical correlation. This involves making additional tests to demonstrate satisfaction of criteria to show that a correlation is in fact a causation as well. Causal inference is the automation of such tests.

In this way, causal inferences using data or results from different models may be identified.

Using the specific example of clinical trials as scientific research, there are at least two specific goals. The first goal is extrapolation. Specifically, usually an earlier stage clinical trial will have a smaller sample size than a subsequent clinical trial, which in turn has a smaller sample size from release to the general public. Accordingly, an experimenter would be interested in understanding how information from a smaller sample size could be extrapolated to project and predict results on a larger sample size. Relating data from other experiments using category theory would increase the sample size and enable extrapolation.

The second goal is particularization. Where a clinical trial covers a relatively large sample size, an experimenter is interested in what would be the likely outcome on a specific individual. For example, a trial can show a result of a sample of 65+ year old non-smoking males with type two diabetes. However, the experimenter would be interested in determining the results for a specific individual, i.e., particularizing to an individual who not only is a 65+ year old non-smoking male with type two diabetes, but also is African American and has a body mass index of 26. Relating data from other experiments using category theory would increase the sample size and parameters under test and enable particularization.

The preceding example discusses particularization via a causal inference engine including via category theory and spatial web, to a particular person. Note that particularization need not be to a particular individual but generally will be to a class or subclass of patients. However, note that particularization taking to its logical conclusion is personalized medicine, that is the application of medical results customized to a specific patient. Specifically, the causal inference engine may be used to create customized therapies and treatments for a specific patient in a specific state at a specific time. Thus, causal inference engine can enable personalized medicine.

Dimensional Flattening and the Spatial Web

The causal inference engine is also to make use of spatial web techniques including dimensional flattening. The spatial web is the outgrowth of graph database techniques where relations between records, represented as nodes, were stored as links, thereby creating a geometrically related set of records. The benefit of geometric relations is that the geometry could be relied on to determine possible and impossible relationships quickly, and perhaps more importantly to roughly situated related records within a predetermined set of links of one another. Congregating records within a predetermined set of links were sometimes called "clusters" and a cluster could be assigned a semantic interpretation.

Sets of clusters could be used to approximate volumetric shapes called manifolds. In mathematics, a manifold is a many dimensioned shape where the surface is generally continuous. A circle is a 2-dimensional manifold. A sphere is a 3-dimensional manifold. Manifolds can have holes, for example a torus, or a donut shaped shape is a manifold.

In the case of graph databases, a spheroid with a number of records from a graph database defining the spheroids surface is a manifold.

Mathematical manifold theory has a number of techniques to approximate the surface of the manifold with less dimensions. For example, if one gets very close to the surface of a sphere, one could approximate a point on the sphere and items within a predetermined radius with a Euclidean plane. This provides techniques to simplify mathematical analysis.

One benefit is that the data from a graph is not necessarily continuous, but because local areas of a manifold based on data from the graph might be, one could still apply continuous techniques (for example calculus) on the limited local area.

Another benefit is the notion of dimensional flattening. Generally speaking, it is easier to perform mathematical operations using less dimensions. Volume calculations are more complex than surface calculations, which in turn are more complex than linear calculations. Considering that records may have a trillion attributes, each representing a dimension, reducing the number of dimensions under consideration can result in simpler math, less storage, and less computation resources utilized.

Exemplary Platform for Correlation of Heterogenous Models for Causal Inference

A system and methods for a causal inference engine and surrounding infrastructure, together comprised of one or more software and hardware components described herein, are described. In the present exemplar, information around clinical trial data and experimental data around life sciences are received, transformed such that the data may be manipulated to find relations including causal inference relations making use of category theory and spatial web dimensional flattening techniques. The resulting transformed data, and results of the manipulated data are then queried to find causal inferences and related information. While the present discussion is around clinical trial data, it is to be noted that causal inferences may be found using the present causal inference engine for other sets of data, and the discussion around clinical trial data is not intended to be limiting. FIG. 1 is a context diagram 100 of a platform for the correlation of heterogenous models for causal inference.

The causal inference engine receives input data 102 in the form of a model, and of resulting data, i.e., data showing the results of trial runs on subjects. In the case of clinical data, the model is usually in the form of a pharmacokinetic model, generally a mathematical dynamical system comprised of a set of differential equations. The resulting data are trial runs comprised of the vital statistics of various subjects, human or otherwise, showing doses and fidelity to the pharmacokinetic model. Generally, there will also be natural language notes providing context for results in general or for specific trial runs. In other cases, the data might be non-clinical trial data and may describe chemical or pharmacological phenomena.

Because different input data 102 are expected to have different models and different results, it is expected that the input data 102 will also be in different formats. However, the input data 102 needs to be converted into a standard format, called a "normalized attribute vector." In this way, the converted data may be mixed and matched during analysis in a consistent and controlled fashion.

Each incoming input data 102 file is expected to have a set of attributes. If one takes all the unique attributes of all the input data 102 files, one can store these attributes into an ontology store 104. The ontology store 104 then identifies unique attributes, and where attributes are duplicative, the ontology store 104 contains synonyms, that is corresponding names for the same attribute across different formats. The ontology store 104 may also store standardized field definitions, including type, and amount of memory. Examples of field definitions include varchar(20) (a string of up to 20 characters), date/time, integer, floating point number, and Boolean.

The input data 102 is accordingly received by a loader 106 software component. The loader 106 comprises a multi-format parser, in some cases a combinatorial parser and accesses the ontology store 104. Based on the ontology store, the normalized attribute vector for each trial data record is created using at least three sections, the first being a reference for the model of data, the second being attributes about the clinical trial such as date, source, and point of contact, and the third being the trial data itself in the form of a set of attributes normalized according to the ontology store 104.

Note that several software components described herein are depicted in FIG. 1 as software services and/or microservices resident in the cloud. However, this is not to foreclose other embodiments where software components are hosted wholly or in part on servers, discrete computers, or microprocessor chips. Alternative hosting is described in additional detail with respect to FIG. 2.

The loader 106 then stores the records transformed into normalized attribute record format into a clinical trial data store 108. Although the records were originally in heterogenous formats because all records are in the same format, the clinical trial data store 108 is now in a state to be analyzed regardless of source.

The clinical trial data store 108 may be analyzed via spatial web analytic. Specifically, the clinical trial data store 108 may be stored by a spatial web generator 110 software component which loads the data in the clinical trial data store 108 into a graph database 112 (sometimes called a spatial web database). The spatial web generator 110 takes each record in normalized attribute vector format and accesses the model and clinical trial portion to generate connections in the graph web database 112 between the records. Population of the graph database 112 as performed by the spatial web generator 110 is described in further detail with respect to FIG. 4 below.

Data in the clinical trial data store 108 may also be analyzed from a category theory perspective. Category generator 114 is a software component that take each record in normalized attribute vector format and accesses the model portions to identify the mathematical properties of the model used. To be clear, a category is not a set of instances of the same model. Rather, a category instance is the definition of a type of mathematical representation (here a model), where the mathematical operations are similar, such that functors and natural transformations may be identified. In practice, most models will be some sort of monoidal category. The category generator 114 is described in further detail with respect to FIG. 5 below.

Upon identifying categories of the models, the category generator 114 stores the identified categories into a category database 116. Along with identified categories, functors, and natural transformations identified by the category generator are also stored in category database 116. In some cases, categories, functors, and natural transformations may also be hand entered.

Once the data from the clinical trial data store 108 is transformed into a graph database 112 and category database

116, the data may then be queried for causal inferences and other relations. This function is performed by a causal inference engine 118 software component which acts as a general query engine.

The causal inference engine 118 is comprised of at least three software components, a dimension (or dimensional) flattening engine 120, a machine learning engine 122, and a report generator 124. The causal inference engine 118 receives queries either programmatically or from a user and provides responses. Performance of queries is described in further detail with respect to the report generator 124 below.

The dimension flattening engine 120 is a software component that reviews data in the graph database 112 and identifies attributes that can be eliminated for purposes of approximating analysis. Specifically, it removes attributes that are unused, and then identifies attributes that if removed, create the least amount of change according to a predetermined optimization function.

The machine learning engine 122 is a software component configured to analyze data in the clinical trial data store 108, the graph database 112, and/or the category database 116. The machine learning engine 122 makes use of machine learning/cognitive network analysis to identify patterns. In particular, the machine learning engine 122 is able to recognize patterns as suggested by category theory, as simplified using dimensional flattening, and to find analogous patterns between the normalized attribute vector representation in the clinical trial data store 108, the category representation in the category database 116, and the graph database 112.

The report generator 124 is a software component that enables both predetermined and ad hoc query capability. The report generator 124 may receive queries and respond to queries either programmatically via APIs or via an interactive query tool. Specifically, the report generator 124 receives queries for either a particular clinical trial, or type of clinical trial, and can return related categories of clinical trials, related clinical trials (as suggested by categories), or amalgamations of results from related clinical trials. In this way, a user may either perform the amalgamation manually or may rely on the causal inference engine 118 to perform the amalgamation.

Figure 2:
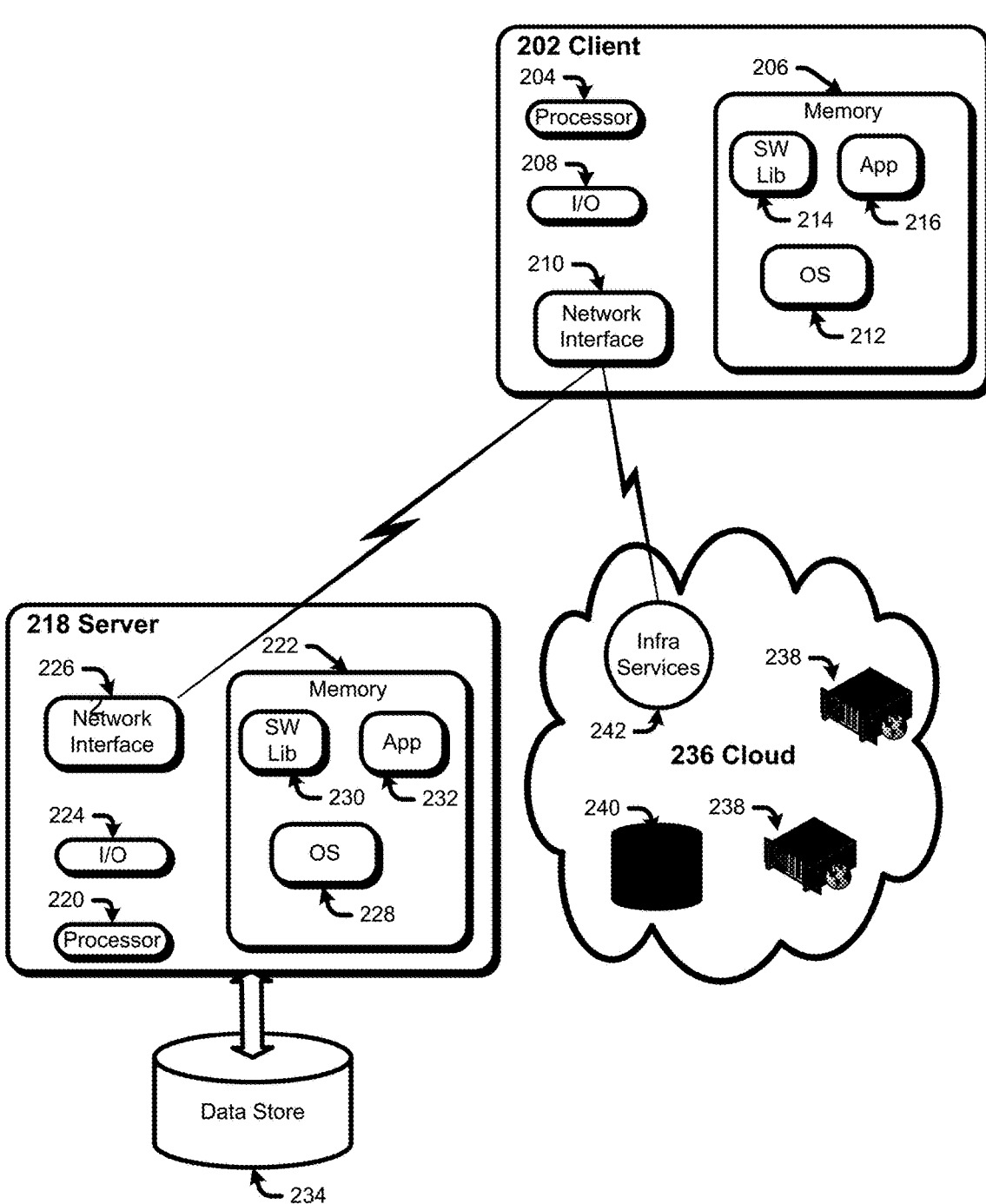
FIG. 2 is a diagram of an exemplary environment for correlation of heterogenous models for causal inference.

Exemplary Environment for Correlation of Heterogenous Models for Causal Inference Before describing a Causal Inference Engine using correlation of heterogenous models, via FIG. 2, we describe in a diagram 200 an exemplary hardware, software, and communications computing environment. Specifically, the functionality for correlating heterogenous data and performing causal inference is generally hosted on a computing device. Exemplary computing devices include without limitation personal computers, laptops, embedded devices, tablet computers, smart phones, and virtual machines. In many cases, computing devices are to be networked.

One computing device may be a client computing device 202. The client computing device 202 may have a processor 204 and a memory 206. The processor may be a central processing unit, a repurposed graphical processing unit, and/or a dedicated controller such as a microcontroller. The client computing device 202 may further include an input/output (I/O) interface 208, and/or a network interface 210. The I/O interface 208 may be any controller card, such as a universal asynchronous receiver/transmitter (UART) used in conjunction with a standard I/O interface protocol such as RS-232 and/or Universal Serial Bus (USB). The network interface 210, may potentially work in concert with the I/O interface 208 and may be a network interface card supporting Ethernet and/or Wi-Fi and/or any number of other physical and/or datalink protocols.

Memory 206 is any computer-readable media which may store software components including an operating system 212, software libraries 214, and/or software applications 216. In general, a software component is a set of computer executable instructions stored together as a discrete whole. Examples of software components include binary executables such as static libraries, dynamically linked libraries, and executable programs. Other examples of software components include interpreted executables that are executed on a run time such as servlets, applets, p-Code binaries, and Java binaries. Software components may run in kernel mode and/or user mode.

Computer-readable media includes, at least, two types of computer-readable media, namely computer storage media and communications media. Computer storage media includes volatile and non-volatile, removable, and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transmission mechanism. As defined herein, computer storage media does not include communication media.

A server 218 is any computing device that may participate in a network. The network may be, without limitation, a local area network ("LAN"), a virtual private network ("VPN"), a cellular network, or the Internet. The server 218 is similar to the host computer for the image capture function. Specifically, it will include a processor 220, a memory 222, an input/output interface 224, and/or a network interface 228. In the memory will be an operating system 228, software libraries 230, and server-side applications 232. Server-side applications include file servers and databases including relational databases. Accordingly, the server 218 may have a data store 234 comprising one or more hard drives or other persistent storage devices.

A service on the cloud 236 may provide the services of a server 218. In general, servers may either be a physical dedicated server, or may be embodied in a virtual machine. In the latter case, the cloud 236 may represent a plurality of disaggregated servers which provide virtual application server 238 functionality and virtual storage/database 240 functionality. The disaggregated servers are physical computer servers, which may have a processor, a memory, an I/O interface and/or a network interface. The features and variations of the processor, the memory, the I/O interface and the network interface are substantially similar to those described for the server 218. Differences may be where the disaggregated servers are optimized for throughput and/or for disaggregation.

Cloud 236 services 238 and 240 may be made accessible via an integrated cloud infrastructure 242. Cloud infrastructure 242 not only provides access to cloud services 238 and 240 but also to billing services and other monetization services. Cloud infrastructure 242 may provide additional service abstractions such as Platform as a Service ("PAAS"), Infrastructure as a Service ("IAAS"), and Software as a Service ("SAAS").

Exemplary Normalized attribute Vector

Figure 3:
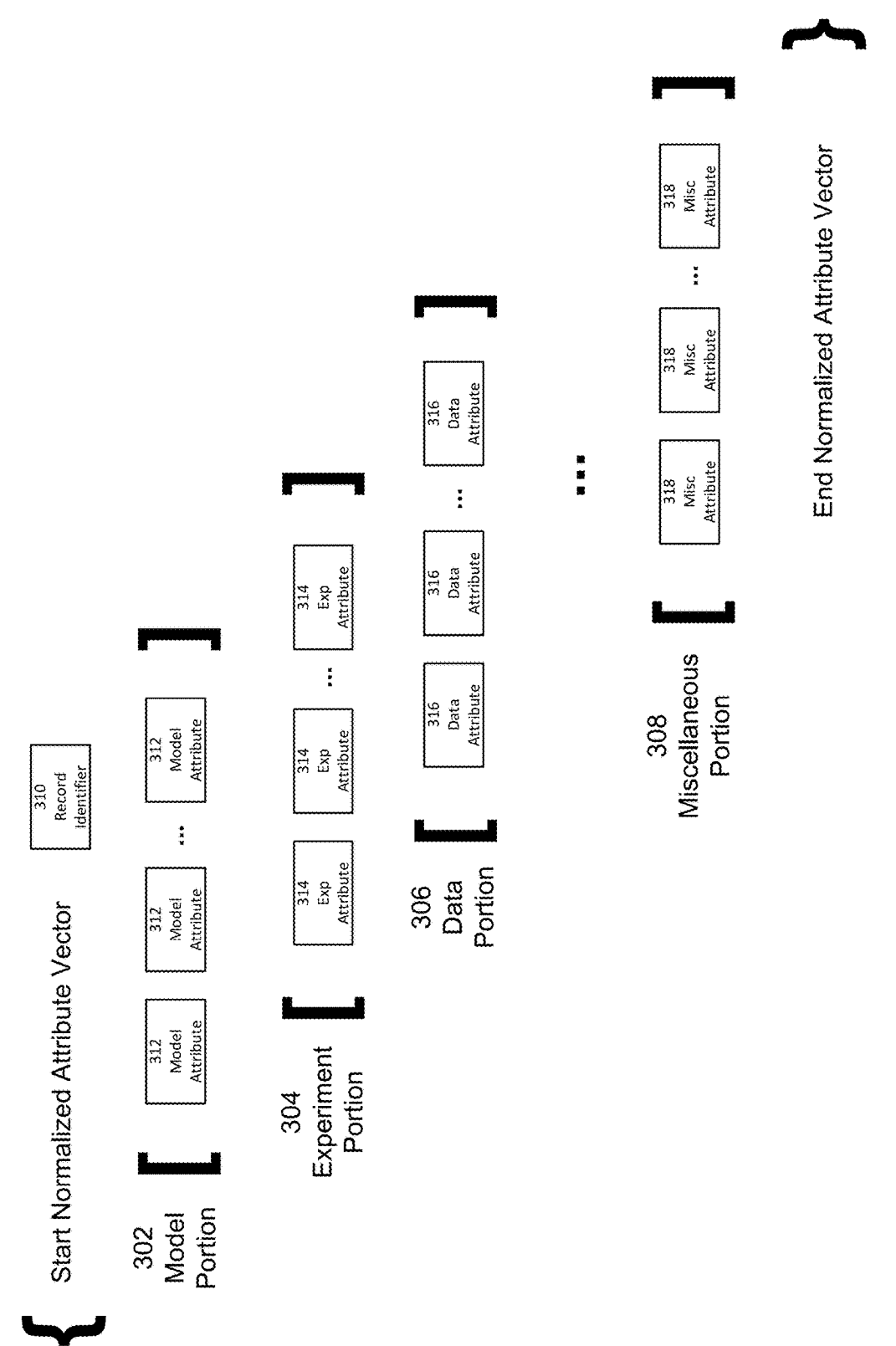
FIG. 3 is a diagram of an exemplary normalized attribute vector.

FIG. 3 illustrates an exemplary normalized attribute vector 300. The normalized attribute vector 300 store a set of attributes that describe a record from an arbitrary clinical trial or experimental results. An attribute is a key-value pair where the attribute name represents the key, and some data represents the value. The data may also be a reference to a value rather than the value itself. The attribute names are taken from the data in the ontology data store 104.

The normalized attribute vector 300 is comprised of a plurality of attributes. There may be a very large set of potential attributes. In some cases, there may be trillions of attributes. However, it is not the case that all attributes will have assigned values. To organize the attributes, there are four portions of the normalized attribute vector 300. First there is a model portion 302 which contains attributes describing the mathematical or pharmacokinetic model used for the record associated with the normalized attribute vector 300. Then there is an experiment portion 304 which contains attributes describing the experiment and the circumstances of the experiment. Next there is a data portion 306 which provides values representing the experimental results of a trial or experimental run. Finally, there is a is a miscellaneous portion 308, which contains any additional attributes reported.

First there is a normalized attribute vector identifier attribute 310. The identifier attribute 310 is a value guaranteed to be unique. Such a value may be generated by a sequential iterator (e.g., a monotonically increasing integer generator creating 1, 2, 3 . . . ) or by a globally unique identifier (GUID) generator.

The model portion 302 contains enough information in the form of model attributes 312 to determine whether the model in the record corresponding to the normalized attribute vector 300 has the same mathematical characteristics of another model, and therefore should be considered in the same category. Some pharmacokinetic models are comprised of various sets of ordinary differential equations. Others make use of partial differential equations. Some models are container based and others are not. Model attributes 312 describe these aspects and other aspects of a model (or provide references to review the model) as to enable the identification of a predetermined category, to assign the model in the record corresponding to the normalized attribute vector 300 to that category, and then to identify functors and potentially natural transformations associated with the category for application to the model in the record corresponding to the normalized attribute vector 300.

The experiment portion 304 contains enough information in the form of experiment attributes 314 to determine patterns about ensuring the various experiments have similar design and were performed under similar circumstances. Experiment attributes 314 may identify one or more protocols (biological workflows), in the form of steps. Other experiment attributes 314 may identify labs where performed, parties involved in performance, date/time, and other environment aspects. The data in the experiment attributes 314 enable a machine learning engine 122 to identify patterns in data. For example, a machine learning engine 122 might identify a specific lab as having particular accurate and easily reproducible results.

The data portion 306 contains data actual data results in the form of data attributes 316 for a particular trial or experimental run. The data attributes 316 have attribute names taken from the ontology data store 104. Where a particular attribute is not used, the value is set to "not applicable" (as opposed to zero which may be valid value). In this way, one can identify applicable attributes during dimensional flattening.

The miscellaneous portion 308 contains miscellaneous attributes 318 that provide additional information for context. For example, an attribute labeled "Error" may indicate that the test result was based on an erroneously executed run. Another attribute label "Comment" may be a natural language value containing contextual notes. In some cases, the machine learning engine 122 may perform natural language analysis on such natural language attribute values to detect patterns.

Figure 4:
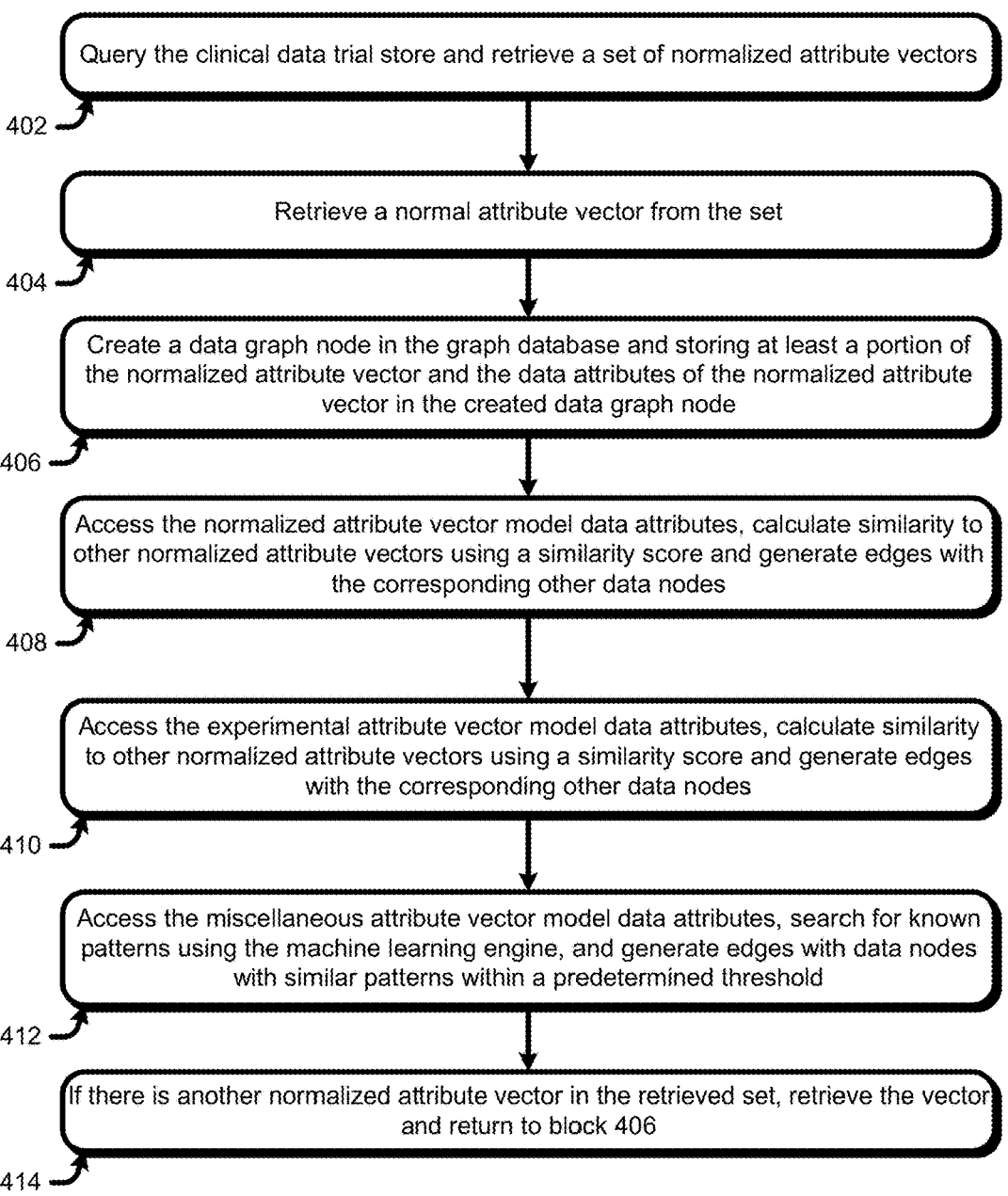
FIG. 4 is a flow chart for creating a graph database from normalized attribute vectors.

Exemplary Method for Correlation of Heterogenous Models for Causal Inference—Graph Database Instance Generation FIG. 4 is a flow chart 400 that shows the manipulation of normalized attribute vectors 300 as stored in the clinical trial data store 108. Specifically, FIG. 4 is a flow chart illustrating an exemplary method for generating a graph database 112 from normalized attribute vectors 300 by the spatial web generator 110.

Turning to FIG. 4, the goal is to take a queried set of normalized attribute records and create a graph database instance stored in graph database 112. Note that graph database 112 can store multiple instances of graph databases. Here we create a new graph database instance. This involves creating data nodes and edges between the data nodes for that instance. In flow chart 400, the edges will be based on manipulation of data stored in the model attributes 302, experiment attributes 304, and miscellaneous attributes 308 of a normalized attribute vector 300.

In block 402, the clinical data trial store 108 is queried according to a set of parameters. If the clinical data trial store 108 is a relational database, with attributes representing fields, the query may be in the form of a structured query language query with parameters referring to fields. Upon execution of the query, a set of normalized attribute vectors is returned in the form of a SQL recordset.

In block 404, the SQL recordset is iterated through. Specifically, a cursor iterated through the records corresponding to normalized attributed vectors one by one. The record, which is comprised of a normalized attribute vector, that is pointed to by the cursor is retrieved or otherwise accessed.

In block 406, a data node in the graph database is added storing at least a portion of the normalized attribute vector 300. In actual practice, only the unique normalized attribute vector identifier 310 is stored. To access attributes of the normalized attribute vector 300, the identifier 310 is used to access attributes to the record stored in the clinical trial data store 108.

In block 408, the model data attributes 302 of the normalized attribute vector 300 just added are retrieved and compared with the model data attributes 302 of all nodes already in the graph database instance. The comparison is performed using a similarity score. If the similarity score is within a predetermined threshold, then an edge between the new node and the existing node in the graph database instance is created.

In block 410, operation is similar as in block 408, except here the experimental data attributes 304 are accessed. As in block 408, the attributes themselves may be compared according to a similarity score and if the similarity score is within a predetermined threshold, then an edge between the new node and the existing node in the graph database instance is created.

In block 412, operation is similar as in blocks 408 and 410, except here the miscellaneous data attributes 308 are accessed. However here, because free form natural language is used, machine learning from the machine learning engine 122 is applied to the natural language fields to identify pattern types. When comparing natural language attributes, where the identified pattern type from the machine learning engine 122 is within a predetermined threshold, then an edge between the new node and the existing node in the graph database instance is created.

In block 414, the cursor is incremented and the recordset is accessed to determine if there is another normalized attribute vector. If there is, then operation returns to block 406. Otherwise, the operation terminated. The result is a graph database instance populated with references to the normalized attributed vectors from the recordset, and edges created based on model attributes 302, experiment attributes 304, and comment and other attributes in the miscellaneous attributes 308.

Method for Correlation of Heterogenous Models for Causal Inference—Category Identification Turning to FIG. 5, FIG. 5 is a flow chart 500 that shows the manipulation of normalized attribute vectors 300 as stored in the clinical trial data store 108 to identify categories by the category generator 114. Note that the category database 116 stores categories, functors, and natural transformations. Note further that the category database 116 can also create different instances of category databases, each corresponding to some subset of normalized vector attributes. The goal is to take a normalized attribute vector 300 that is not associated with a category, and to either associate it with a category in the category database 116, or if an appropriate category does not exist, create one in the category database and then associate the normalized attribute vector 300 with the newly created category. For categories stored in the category database 116, each stored category may be associated with a set of model attributes that can be used to comparison purposes when determining whether a normalized attribute vector 300 should be associated with that category.

In block 502, a normalized attribute vector 300 is retrieved. As with blocks 402 and 404, the normalized attribute vector 300 may be part of a recordset retrieved via a SQL query from the clinical trial data store 108 or may simply be a standalone record.

In block 504, the model attributes 302 of the retrieved normalized attribute vector 300 are accessed. Since the model attributes 302 describe the mathematical and/or pharmacokinetic model used, these model attributes 302 may be used to determine a category.

In block 506, the model attributes 302 of the retrieved normalized attribute vector 300 are compared to attributes associated to the various categories in the category database 116. If a category is found, in block 508, the normalized attribute vector 300 is associated with the category. In practice, the category database 116 will not store the full normalized attribute vector 300, but instead will only store the vector identifier 310.

If a category is not found, in block 510 a new category is created in the category database 116. As stated above, stored categories are associated with attributes. Here the attributes associated with the new category are based at least in part on the attributes of the normalized attribute vector 300 under analysis.

Note that the in block 510, the newly created category is not necessarily yet named. At some future time, a name may be manually added, or automatically associated via machine learning.

At the end of this process 500, the result is a category database instance with a full set of categories, each category associated with attributes, and each category associated with at least identifiers of a set of normalized attribute vectors 300. Over time, functors and natural transformations will be identified and added to the category database 116. At that point, in conjunction with graph database 112, causal inferences on the thereby correlated heterogenous models may be performed.

Conclusion

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system to perform data correlation of data from heterogenous models and infer causation, the system comprising:

a computer processor;

a memory configured to store computer readable instructions and computer readable data;

an ontology store database stored in the memory, configured to store synonym information for data attributes;

a loader software component stored in the memory and configured to receive input data and to receive data attribute synonym information from the ontology store database and, based at least on the received data attribute synonym information, configured to create normalized attribute vectors from the input data;

a clinical trial data store stored in the memory, configured to receive and store normalized attribute vectors from the loader software component;

a spatial web generator software component stored in the memory and a graph database stored in the memory, wherein the spatial web generator component is configured to:

retrieve a plurality of normalized attribute vectors from the clinical trial data store, the normalized attribute vectors each comprising a plurality of normalized attribute vector data attributes that include mathematical model attributes of heterogenous models, create, in the graph database, graph data nodes configured to store respective normalized attribute vectors, each normalized attribute vector stored in a respective graph data node, for each of the normalized attribute vectors, store at least a portion of the normalized attribute vector and the normalized attribute vector data attributes in a respective graph data node in the graph database, generate a graph database edge between the graph data node of a first normalized attribute vector having normalized attribute vector data attributes of a first mathematical model and the respective graph data node of at least one other normalized attribute vector having normalized attribute vector data attributes of a second mathematical model, the first and second mathematical models being heterogenous, based at least on some of the normalized attribute vector data attributes in the first normalized attribute vector and the respective at least one other normalized attribute vector, calculate a similarity score between at least two of the retrieved normalized attribute vectors, wherein the generating the graph database edge between the graph data node and the respective graph data node for at least one other normalized attribute vector is based on the calculated similarity score, and based at least on the calculated similarity score, store at least some data from the normalized attribute vectors into the graph data node of the graph database with an association from which causation in the data is inferred.

2. The system of claim 1, wherein the loader software component is configured to receive input files in a plurality of formats, and wherein the loader includes a multi-format parser.

3. The system of claim 2, wherein the multi-format parser is a combinatorial parser.

4. The system of claim 1, wherein the ontology store database is configured to store standardized field definitions for data attributes, and the loader software component is configured to assign a standardized field definition from the ontology to a normalized attribute vector.

5. The system of claim 1, wherein the normalized attribute vector is configured to store mathematical model information and experimental data for clinical trials.

6. The system of claim 1, further comprising a category generator software component stored in the memory and a category database stored in the memory, wherein the category generator software component is configured to retrieve a plurality of normalized attribute vectors from the clinical trial data store, identify mathematical categories from the normalized attribute vectors, and based at least on the identified mathematical categories store at least some data from the normalized attribute vectors into the category database.

7. The system of claim 6, further comprising a causal inference engine software component stored in the memory, configured to receive data from the category database, and to perform inferences on at least some of the received data.

8. The system of claim 1, wherein the causal inference engine software component is configured to receive graph data from the graph database, and to perform inferences on at least some of the received graph data.

9. The system of claim 1, wherein at least a portion of the system has functionality exposed via microservices.

10. A method to load a graph database, comprising:

receiving at a spatial web generator software component a normalized attribute vector from a clinical trial database, the normalized attribute vector comprised of a plurality of normalized attribute vector data attributes of a first mathematical model;

at the spatial web generator software component, creating in a graph database graph data nodes, the graph database storing a plurality of other normalized attribute vectors, each other normalized attribute vector stored in a respective graph data node;

at the spatial web generator software component, storing at least a portion of the normalized attribute vector and the normalized attribute vector data attributes in the created graph data node;

at the spatial web generator software component, generating a graph database edge between the graph data node and the respective graph data node for at least one other normalized attribute vector, based at least on some attributes in the received normalized attribute vector and the respective other normalized attribute vector; and storing the received normalized attribute vector in the created graph data node.

11. The method of claim 10, further comprising, at the spatial web generator software component, calculating a similarity score for the normalized attribute vector with respect to at least one other normalized attribute vector; wherein the generating the graph database edge between the graph data node and the respective graph data node for at least one other normalized attribute vector is based on the calculated similarity score.

12. The method of claim 11, wherein the similarity score is based on experiment attributes in the normalized attribute vector and experiment attributes in the at least one other normalized attribute vector.

13. The method of claim 10, further comprising, at the spatial web generator software component, searching for patterns within miscellaneous attributes in a plurality of normalized attribute vectors in the graph database with a machine learning software component, including the normalized attribute and the at least one other normalized attribute vector, wherein the miscellaneous attributes are attributes that are not mathematical model attributes, experiment attributes, or experiment data attributes.

14. The method of claim 10, wherein the generating the graph database edge between the graph data node and the respective graph data node for at least one other normalized attribute vector is based on the received normalized attribute vector and the other normalized attribute vector having similar patterns within a predetermined threshold.

15. A method to infer causation in data from heterogenous mathematical models, comprising:

associating a normalized attribute vector to a mathematical category in a category database, the associating comprising:

selecting, at a category generator software component, a normalized attribute vector, the normalized attribute vector comprised of a plurality of data attributes including mathematical model attributes;

at the category generator software component, searching within a category database for a pre-existing mathematical category corresponding to the mathematical model attributes of the normalized attribute vector;

determining, from the search, that the category database contains a pre-existing mathematical category corresponding to the mathematical model attributes of the normalized attribute vector; and in response to determining that the category database contains a pre-existing mathematical category corresponding to the mathematical model attributes of the normalized attribute vector, performing a category association in the category database, including associating the returned mathematical category with the normalized attribute vector; and storing the association in the category database; and loading a graph database, comprising:

receiving, at a spatial web generator software component a normalized attribute vector from a clinical trial database, the normalized attribute vector comprised of a plurality of normalized attribute vector data attributes of a first mathematical model;

at the spatial web generator software component, creating, in a graph database, graph data nodes, the graph database storing a plurality of other normalized attribute vectors, each other normalized attribute vector stored in a respective graph data node and having normalized attribute vector data attributes of a second mathematical model, the first and second mathematical models being heterogenous;

at the spatial web generator software component, storing at least a portion of the received normalized attribute vector and the normalized attribute vector data attributes in the created graph data node;

at the spatial web generator software component, generating a graph database edge between the graph data node and the created graph data node for at least one other normalized attribute vector, based at least on some attributes in the received normalized attribute vector and the respective other normalized attribute vector;

storing the received normalized attribute vector in the created graph data node; and inferring causation in the normalized attribute vector data attributes of the received normalized attribute vector and the normalized attribute vector data attributes of the other normalized attribute vectors, based on the association of the returned mathematical category with the normalized attribute vector.

16. The method of claim 15, wherein the association of the normalized attribute vector and the returned category is via a reference to an identifier of the normalized attribute vector as stored in an external database.

17. The method of claim 15, further comprising:

determining, from the search, that the category database contains a pre-existing mathematical category corresponding to the mathematical model attributes of the normalized attribute vector;

in response to determining that the category database contains no pre-existing mathematical category corresponding to the mathematical model attributes of the normalized attribute vector, generating at the category generator software component a mathematical category corresponding to the mathematical model attributes of the normalized attribute vector, and storing the generated mathematical category in the category database; and performing a category association in the category database including associating the generated mathematical category with the normalized attribute vector and storing the association in the category database.

18. The method of claim 17, wherein the association of the normalized attribute vector and the returned category is via a reference to an identifier of the normalized attribute vector as stored in an external database, rather than a copy of the normalized attribute vector in the category database.

19. The method of claim 16, further comprising:

via a machine learning generation routine at the category generator software component, generating a name for the generated mathematical category, associating the generated name with the generated mathematical category, and storing the association of the generated name with the generated mathematical category in the category database.

* * * * *